United States Patent [19]

Landis et al.

[11] Patent Number: 5,687,715

[45] Date of Patent: *Nov. 18, 1997

[54] NASAL POSITIVE AIRWAY PRESSURE APPARATUS AND METHOD

[76] Inventors: Robert M. Landis, 1130 Puddingstone Rd., Mountainside, N.J. 07092; Wayne W. Disanza, 887 Derry Dr., Toms River, N.J. 08753

[*] Notice: The portion of the term of this patent subsequent to Feb. 17, 2013, has been disclaimed.

[21] Appl. No.: 577,181

[22] Filed: Dec. 22, 1995

Related U.S. Application Data

[63] Continuation-in-part of Ser. No. 155,479, Nov. 19, 1993, Pat. No. 5,477,852, which is a continuation-in-part of Ser. No. 19,993, Feb. 17, 1993, Pat. No. 5,269,296, which is a continuation of Ser. No. 784,371, Oct. 29, 1991, abandoned.

[51] Int. Cl.$^6$ ........................................ A61M 16/00
[52] U.S. Cl. .................. 128/207.18; 128/207.15; 128/204.18; 604/94; 606/192
[58] Field of Search .............. 128/DIG. 26, 911, 128/912, 207.15–207.18, 204.11, 204.12, 204.18, 200.24, 200.26, 201.22, 203.21, 205.25; 604/94; 606/191, 192, 196

[56] References Cited

U.S. PATENT DOCUMENTS

| | | | |
|---|---|---|---|
| 812,706 | 2/1906 | Warbasse | 128/207.13 |
| 1,158,780 | 11/1915 | Bolton | 128/207.13 |
| 1,176,886 | 3/1916 | Ermold | 128/207.13 |
| 1,206,045 | 11/1916 | Smith | 128/206.24 |

(List continued on next page.)

FOREIGN PATENT DOCUMENTS

| | | |
|---|---|---|
| 4010975 | 10/1991 | Germany. |
| 220978 | 6/1968 | Sweden. |
| 1250307 | 8/1986 | U.S.S.R. |
| 1255128 | 9/1986 | U.S.S.R. |
| WO8203548 | 10/1982 | WIPO. |
| 9220392 | 11/1992 | WIPO. |

OTHER PUBLICATIONS

"Management of Chronic Alveolar Hyperventilation with Nasal Positive Pressure Breathing"; DiMarco, et al; Chest: 92/5/952–954 Nov. 1987.

Benefit of Nasal CPAP in Obstructive Sleep Apnea is Due to Positive Pharyngeal Pressure; N.C. Abbey, K.R. Cooper and J.A. Kwentus; Sleep 12 (5) 420–422 (1989).

Long–Term Compliance with Nasal Continuous Positive Airway Pressure Therapy of Obstructive Sleep Apnea; R.E. Waldhorn, T.W. Herrick, M.C. Nguyen, A.E. O'Donnell, J. Sodero, and S.J. Potolicchio; Chest 1990; 97:33–38.

Obstructive Sleep Apnea Treated by Independently Adjusted Ispiratory and Expiratory Positive Airway Pressures via Nasal Mask; M.H. Sanders, N. Kern; Chest 1990; 98:317–24.

Surgical Treatment of Obstructive Sleep Apnea: Is Mandibular Surgery an Advance?; Chest 1990; 98:1315–16.

Maxillofacial Surgery and Nasal CPAP: A Comparison of Treatment for Obstructive Sleep Apnea Syndrome; R.W. Riley, N.B. Powell and C. Guilleminault; Chest 1990; 98:1421–25.

The Effect of Nightly Nasal CPAP Treatment on Underlying Obstructive Sleep Apnea and Pharyngeal Size; N.A. Collop, A.J. Block and D. Hellard; Chest 1991; 99:855–60.

(List continued on next page.)

*Primary Examiner*—Vincent Millin
*Assistant Examiner*—Eric P. Raciti

[57] ABSTRACT

A nasal positive airway pressure device is provided having a plenum chamber, a pair of nasal delivery members, and a variable orifice venting aperture member. The variable orifice venting aperture member preferably is mounted to the plenum chamber, but may be mounted at other locations in communication with the nasal delivery members. The variable orifice vent aperture member expands under increased pressure, e.g., during exhalation, and contracts to its original diameter at lower pressures, e.g., during inhalation, to provide variable venting capacity during positive airway pressure treatment.

20 Claims, 6 Drawing Sheets

U.S. PATENT DOCUMENTS

| | | | |
|---|---|---|---|
| 1,632,449 | 6/1927 | McKesson | 128/206.24 |
| 2,185,997 | 1/1940 | Heidbrink | 128/204.29 |
| 2,245,969 | 6/1941 | Francisco | 128/207.18 |
| 2,259,817 | 10/1941 | Hawkins | 128/207.18 |
| 2,493,326 | 1/1950 | Trinder | 606/196 |
| 2,931,358 | 4/1960 | Sheridan | 128/207.18 |
| 3,481,339 | 12/1969 | Puig | 128/207.15 |
| 3,516,407 | 6/1970 | Ruggero | 606/196 |
| 3,566,862 | 3/1971 | Schuh | 601/44 |
| 3,568,678 | 3/1971 | Pourquier | 604/174 |
| 3,640,282 | 2/1972 | Kamen | 128/207.15 |
| 3,683,907 | 8/1972 | Cotabish | 128/200.28 |
| 3,707,151 | 12/1972 | Jackson | 128/207.15 |
| 3,766,924 | 10/1973 | Pidgeon | 606/196 |
| 3,794,036 | 2/1974 | Carroll | 128/207.15 |
| 3,850,176 | 11/1974 | Gottschalk | 606/196 |
| 3,856,051 | 12/1974 | Bain | 138/114 |
| 3,903,893 | 9/1975 | Scheer | 606/196 |
| 4,056,104 | 11/1977 | Jaffe | 128/207.15 |
| 4,090,518 | 5/1978 | Elam | 128/207.15 |
| 4,106,505 | 8/1978 | Salter | 128/207.18 |
| 4,151,843 | 5/1979 | Brekke | 128/205.25 |
| 4,156,426 | 5/1979 | Gold | 128/204.18 |
| 4,178,937 | 12/1979 | Taylor | 604/103 |
| 4,216,769 | 8/1980 | Grimes | 128/207.13 |
| 4,235,239 | 11/1980 | Elam | 128/207.15 |
| 4,273,124 | 6/1981 | Zimmerman | 128/207.18 |
| 4,367,735 | 1/1983 | Dali | 128/207.18 |
| 4,422,456 | 12/1983 | Tiep | 128/207.18 |
| 4,465,067 | 8/1984 | Koch | 128/207.18 |
| 4,538,606 | 9/1985 | Whited | 128/207.15 |
| 4,598,707 | 7/1986 | Agdanowski | 128/207.15 |
| 4,655,213 | 4/1987 | Rapoport et al. | 128/205.25 |
| 4,753,233 | 6/1988 | Grimes | 128/207.18 |
| 4,782,832 | 11/1988 | Trimble | 128/207.18 |
| 4,790,308 | 12/1988 | Weichselbaum | 128/207.18 |
| 4,818,320 | 4/1989 | Weichselbaum | 156/227 |
| 4,836,200 | 6/1989 | Clark | 128/207.18 |
| 4,915,105 | 4/1990 | Lee | 128/205.27 |
| 5,024,220 | 6/1991 | Holmgreen et al. | 128/207.18 |
| 5,042,478 | 8/1991 | Kopala | 128/207.18 |
| 5,065,756 | 11/1991 | Rapoport | 128/204.18 |
| 5,105,807 | 4/1992 | Kahn et al. | 128/207.18 |
| 5,139,510 | 8/1992 | Goldsmith, III et al. | 606/196 |
| 5,148,802 | 9/1992 | Sanders et al. | 128/204.18 |
| 5,161,525 | 11/1992 | Kimm et al. | 128/204.26 |
| 5,199,424 | 4/1993 | Sullivan et al. | 128/204.18 |
| 5,245,995 | 9/1993 | Sullivan et al. | 128/204.23 |
| 5,269,296 | 12/1993 | Landis | 128/207.18 |
| 5,477,852 | 12/1995 | Landis et al. | 128/207.18 |

OTHER PUBLICATIONS

The Effect of Positive Reinforcement on Hourly Compliance in Nasal Continuous Positive Airway Pressure Users with Obstructive Sleep Apnea; E.C. Fletcher and R.A. Luckett; Am. Rev. Respir. Dis. 1991; 143:936–941.

Nasal Continuous Positive Airway Pressure Facilities Respiratory Muscle Function During Sleep in Severe Chronic Obstructive Pulmonary Disease; B.J. Petrof, R.J. Kimoff, R.D. Levy, M.G. Cosio and S.B. Gottfried; Am. Rev. Respir. Dis. 1991; 143:928–935.

Efficacy of Nocturnal Nasal Ventilation in Patients with Restictive Thoracic Disease; N.S. Hill, S.E. Eveloff, C.C. Carlisle and S.G. Goff; Am. Rev. Respir. Dis. 1992; 145:365–371.

Nocturnal Nasal Intermittent Positive Pressure Ventilation with Bi-Level Positive Airway Pressure (BiPAP) in Respiratory Failure; R.E. Waldhorn; Chest 1992; 101:516–521.

Physiologic Evaluation of Pressure Support Ventilation by Nasal Mask in Patients with Stable COPD; Chest 1992; 101:385–91.

"Softwear ™ Nasal Mask"; Lifecare; ©1991.

New Product News–Companion 318 Nasal CPAP System from Puritan–Bennett.

Harmonization and the Work of Breathing: For Bi–Level Respiratory Therapy; Puritan–Bennett.

Companion® Adam Nasal CPAP Circuit.

New Mask Fitting Program for Health Care Professionals; Night Times; Jun. 1993.

The BiPap® System Compensates for Leaks; Respironics, Inc., ©1993.

Why Mask Leaks Are No Longer a Problem; Respironics, Inc., ©1993.

"The Sullivan™ Mask System" (undated).

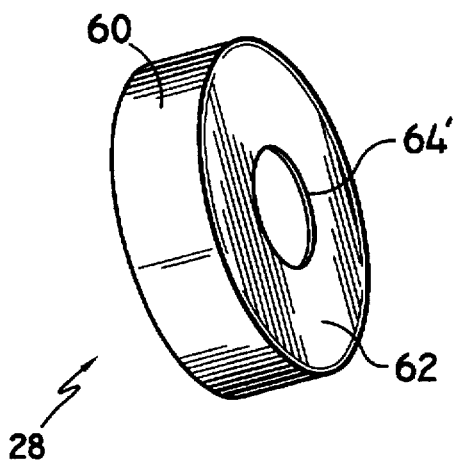
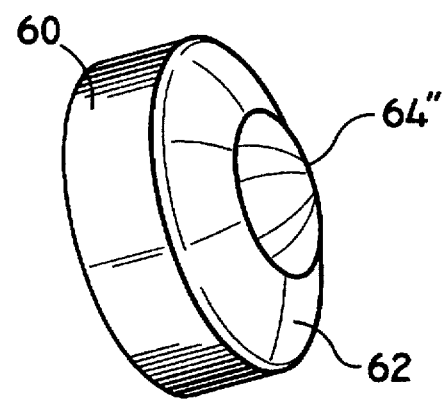
FIG. 7A  FIG. 7B
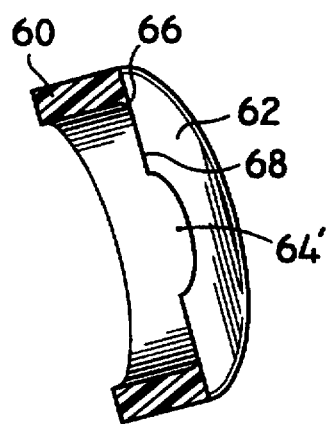
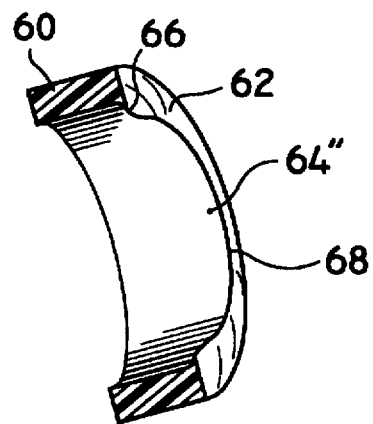
FIG. 7C  FIG. 7D

NASAL POSITIVE AIRWAY PRESSURE APPARATUS AND METHOD

RELATED APPLICATIONS

This application is a continuation-in-part of U.S. patent application Ser. No. 08/155,479, filed Nov. 19, 1993, now U.S. Pat. No. 5,477,852, which is a continuation-in-part of U.S. patent application Ser. No. 08/019,993, filed Feb. 17, 1993, now U.S. Pat. No. 5,269,296, which is a continuation of U.S. patent application Ser. No. 07/784,371, filed Oct. 29, 1991, now abandoned. The disclosures of the foregoing patents and applications are incorporated herein by reference in their entirety.

TECHNICAL FIELD

The present invention relates to an apparatus and method for treating sleep apnea. More specifically, the present invention provides a nasal positive airway pressure device having a variable orifice vent aperture.

BACKGROUND OF THE INVENTION

Obstructive sleep apnea is a condition in which the patient's airway passage is blocked and no air can pass to the lungs during sleep. During a customary sleep period a person suffering from sleep apnea can experience so-called apneic events. Apneic events are periods when the patient's airway becomes blocked, often for ten seconds or more, until the patient rouses from sleep and starts breathing normally again. Those suffering from sleep apnea may experience numerous apneatic events each night, causing a deficiency of restful sleep and, due to depleted oxygen levels, possible long term health problems such as heart ailments.

Continuous positive airway pressure (CPAP) and, more specifically, nasal continuous positive airway pressure (nCPAP) has been shown to be an effective treatment for sleep apnea. See "Benefit of Nasal CPAP in Obstructive Sleep Apnea is Due to Positive Pharyngeal Pressure", N. C. Abbey, K. R. Cooper and J. A. Kwentus, Sleep 1989, 12 (5):420–422; "The Effect of Nightly Nasal CPAP Treatment on Underlying Obstructive Sleep Apnea and Pharyngeal Size", N. A. Collopp. A. J. Block and D. Hellard, Chest 1991, 99:855–860; and "Nasal Continuous Positive Airway Pressure Facilitates Respiratory Muscle Function During Sleep in Severe Chronic Obstructive Pulmonary Disease", B. J. Petrof, R. J. Kimoff, R. D. Levy, M. G. Cosoi and S. B. Gottfried, Am. Rev. Respir. Dis. 1991; 143:928–935. This treatment involves applying a constant supply of gas, typically a mixture of air supplemented with moisture vapor or oxygen, to the nasal passages at a predetermined, slightly elevated pressure in order to prevent negative pressure conditions within the passageway.

More recently, a related form of treatment has been tested and may achieve success similar to nCPAP. In this treatment, known as BiPAP™ therapy, a controller regulates the gas pressure in response to the patient's breathing patterns and supplies positive gas pressure at a first gas pressure during the inspiratory phase, i.e., inhalation by the patient, and supplies gas at a second, reduced pressure during the expiratory phase, i.e., as the patient exhales. The first gas pressure typically corresponds to pressure used in nCPAP treatment and is on the order of about 10 centimeters of water or greater. The second pressure level is about half the first gas pressure, and typically is about 5 to 7 centimeters of water pressure. It has been reported that reducing the gas pressure during exhalation provides increased patient comfort and compliance by reducing the work done by the patient in overcoming the gas pressure during exhalation. BiPAP™ treatment is disclosed in "Obstructive Sleep Apnea Treated by Independently Adjusted Inspiratory and Expiratory Positive Airway Pressures via Nasal Mask", M. H. Sanders and N. Kern,.Chest 1990; 98:317–24; "Nocturnal Nasal Intermittent Positive Pressure Ventilation with Bi-level Positive Airway Pressure (BiPAP) in Respiratory Failure", R. E. Waldhorn, Chest 1992, 101:16–521; "Efficacy of Nocturnal Nasal in Patients with Restrictive Thoracic Disease", Am. Rev. Respir. Disease, 1992; 145:365–371; "Physiologic Evaluation of Pressure Support Ventilation by nasal mask in Patients With Stable COPD", N. Ambrosino, S. Nava, P Bertone, C. Frachia, C. Rampulla, Chest 1992; 101: 385–91. As will be appreciated, BiPAP™ treatment requires sensing and control mechanisms to monitor and adjust treatment gas pressure.

In general, nCPAP and BiPAP™ treatment typically involve placing a mask over the nose of the patient by means of a harness or other headgear and providing a source of positive low pressure air connected to the mask. One such mask is the Sullivan Bubble Mask, available from ResCare, Inc., San Diego, Calif.

U.S. Pat. No. 4,782,832 issued to Trimble, et. al. proposes a device for nCPAP treatment intended as an alternative to conventional mask devices. The Trimble structure has become the accepted apparatus for nCPAP treatment. Trimble discloses a nasal puff adapted to be worn adjacent the nose of the wearer-patient. The nasal device includes a relatively small plenum chamber including structure defining an inlet adapted for coupling with a source of gas, and a pair of spaced apart, separate gas outlets in communication with the inlet. Typically, the plenum chamber is in the form of a generally Y-shaped hollow body with the gas outlets located in the branches of the body. The nasal puff further includes a pair of gas delivery elements each having a gas flow passageway therethrough and respectively operatively coupled with a corresponding gas outlet for conveying gas from the outlet through and out the passageway. Each of the gas delivery elements is configured for insertion into a respective naris of a patient, and for this purpose the outer wall of the elements are generally frustoconically shaped so as to sealingly engage the naris-defining surfaces of the nose. Adjustability of the naris elements is provided by rotatably mounting the elements to the plenum housing and by mounting the elements in slots permitting selective lateral positioning of the elements with respect to each other. Flexible bellows-type corrugated sections can be provided in each of the elements and/or in appropriate positions in the plenum housing so as to add further ranges of flexibility and adjustability. The nares elements are fabricated from relatively soft, deformable, shape-retaining synthetic resin material permitting manual deformation and alteration of the effective shape and position of the elements. Trimble discloses a harness to be worn on a patient's head with flexible mask-retaining straps extending from the main harness strap to each side of the nasal puff. The harness assembly includes an elongated gas-conveying tube which is adapted for coupling with the inlet of the nasal puff and extends upwardly along the length of the bridge of the patient's nose and across the patient's forehead, terminating at the top of the patient's forehead. The tube is longitudinally bifurcated to divide the overall tube and present a pair of elongated, juxtaposed passageways, one of which is connected to a source of pressurized air and the other to a discharge tube for purging patient-generated $CO_2$ during exhalation). In an alternative embodiment Trimble discloses inflatable nares elements that are inserted into the nares and inflated manually by a separate source of pressure.

The Trimble nasal puff and harness assembly is an accepted apparatus for treatment of sleep apnea using nCPAP therapy. While the Trimble device is an improvement over prior mask structures, some patients continue to object to the Trimble structure as uncomfortable to wear. Studies show that a small but significant number of patients fail or are unable to continue nCPAP treatment due in at least some cases to the inconvenience or discomfort of wearing the presently available apparatus. See "The Effect of Positive Reinforcement on Hourly Compliance in Nasal Continuous Positive Airway Pressure Users with Obstructive Sleep Apnea", E. C. Fletcher and R. A. Luckett, Am. Rev. Respir. Dis. 1991; 143:936–941; "Maxillofacial Surgery and Nasal CPAP", R. W. Riley, N. B. Powell, C. Guilleminault, Chest 1990; 98:1421–1425; and "Surgical Treatment of Obstructive Sleep Apnea—Is Mandibular Surgery an Advance?", Chest 1990; 98:1315–1316.

Notwithstanding the general consensus that nasal positive airway pressure is an effective treatment for sleep apnea, a substantial number of patients either cannot tolerate treatment or choose to forego treatment. It is believed a substantial number of such patients could benefit from a nasal positive airway pressure apparatus which is more convenient to use and comfortable to wear, thereby resulting in increased treatment compliance. The device disclosed and claimed herein may find application to either nCPAP or BiPAP treatment.

U.S. Pat. No. 5,269,296 to Landis discloses and claims a nasal airway pressure device having a pair of cannulae. Each cannula has an inflatable cuff in gaseous communication with the cannula lumen such that the cuff is inflated during use to gently but securely position the cannula relative to the sensitive nares walls. The Landis 296 patent also discloses vent holes adjacent the cannulae for relieving excess gas pressure created during exhalation.

U.S. Pat. No. 5,477,852 to Landis and Disanza discloses and claims a nasal airway pressure device including a variable orifice vent hole.

A mask having a valve is proposed in Rapoport U.S. Pat. Nos. 4,655,213 and 5,065,756. A mask with a flap valve is shown in Bolton U.S. Pat. No. 1,158,780.

SUMMARY OF THE DISCLOSURE

In accordance with the present disclosure, a positive nasal airway pressure device is provided for treatment of sleep apnea. The device includes means for securing the device to the patient's head, i.e., a head strap or harness, a primary air tube to be connected to a source of air pressure in a known manner, and a nasal apparatus to deliver pressurized air to the nose of the patient. In accordance with the disclosure, nasal delivery devices are improved by associating one or more variable orifice members with the nasal apparatus or related conduits. The variable orifice member(s) respond to increased air pressure within the device at various stages of operation, e.g., exhalation, to relieve excess pressure. Variable pressure relief may provide increased patient comfort and, hence, greater patient compliance.

In general, the device includes a plenum chamber connected at an inlet port to a source of pressurized air. The plenum chamber also is connected to a pair of nasal delivery members to deliver the pressurized air to the nares of a patient. The nasal delivery members may be a pair of nasal cannulae with inflatable cuffs for positioning the cannulae in the nares of the patient. Alternatively, the nasal delivery members may be generally frustoconical elements made of a soft synthetic material to seat against the openings of the nares.

Preferably, a variable orifice vent aperture member is associated with the plenum to provide relief of pressure as desired. It is contemplated, however, that one or more variable orifice members may be provided in the plenum and/or in one or more of the conduits adjacent the plenum and/or nasal delivery members.

In use, the device is secured to the head of the user with the securing strap or harness. The plenum and nasal delivery elements are adjusted, as appropriate, to comfortably position the nasal delivery members relative to the patient's nares. The source of pressurized air is activated to supply pressurized air to the device via a conduit attached to an inlet port of the plenum. The pressurized air passes through the plenum and enters the patient's nostrils through the nasal delivery members to effect treatment. Where the nasal delivery members are a pair of cannulae each having an associated inflatable cuff, the pressurized air enters the inflatable cuff through at least one aperture through the corresponding cannula wall to inflate the cuff so that the cuff engages the nares walls, thereby holding the cannula in place. In one embodiment, the inflatable cuff extends slightly beyond the end of the cannula to protect the sensitive nare walls from abrasion due to contact with the end of the cannula. During the inspiratory phase, i.e., inhalation, the pressure from the source of pressurized air maintains the cuff inflated and effects treatment.

During the expiratory phase, i.e., exhalation, excess pressure within the device is vented through the variable orifice vent hole(s) associated with the delivery device in proximity to the patient's nose, e.g., located on the conduit, plenum chamber, etc. Because the variable orifice is constructed of an elastic material, the orifice material expands in response to increased gas pressure within the device, thereby increasing the area of the vent orifice hole and temporarily increasing the venting capacity of the orifice. As gas pressure within the device subsides, e.g., as inhalation commences, the elastic material returns to its original configuration with a smaller orifice area or diameter. In this manner, the venting capacity of the variable orifice vent aperture increases during exhalation or under other increased pressure conditions to relieve excess pressure, and returns to its original, reduced aperture size and venting capacity when such increased venting capacity is not required, e.g., during normal inhalation with pressurized gas supplied to the nares. Thus, excess pressure within the device, as may occur during exhalation, can promptly and effectively be relieved, while permitting optimum direction of pressurized air to the nares under normal operating pressure conditions, e.g., inhalation. Because excess gas pressure can contribute to patient discomfort and non-compliance, the effectiveness of treatment may be increased.

The apparatus in accordance with the disclosure provides considerable advantages over existing treatment devices by providing a device which is more comfortable to use. Moreover, because the variable orifice vent aperture automatically adjusts the venting capacity of the device in response to increasing and decreasing pressure within the device, e.g., during inhalation and exhalation, it may be possible to achieve results comparable to BiPAP™ with a simple mechanical device and continuous positive pressure, without complex air pressure monitoring and control systems. These and other advantages of the invention will become apparent to those skilled in the art from the foregoing general description and the following detailed disclosure, and from practice with the invention.

BRIEF DESCRIPTION OF THE DRAWINGS

The disclosure set forth herein can be better understood with reference to the accompanying drawings, which form a part of the disclosure, in which:

FIG. 7A is a perspective view of a variable orifice cap illustrating the orifice defining surface in the first, unexpanded condition to provide a first aperture diameter;

FIG. 7B is a perspective view of the variable orifice cap of FIG. 7A, illustrating the orifice defining surface in a second, expanded condition to provide a second, enlarged aperture diameter;

FIG. 7C is a sectional view, in perspective, of the variable orifice cap of FIG. 7A; and FIG. 7D is a sectional view, in perspective, of the variable orifice cap of FIG. 7B.

Figure 1:
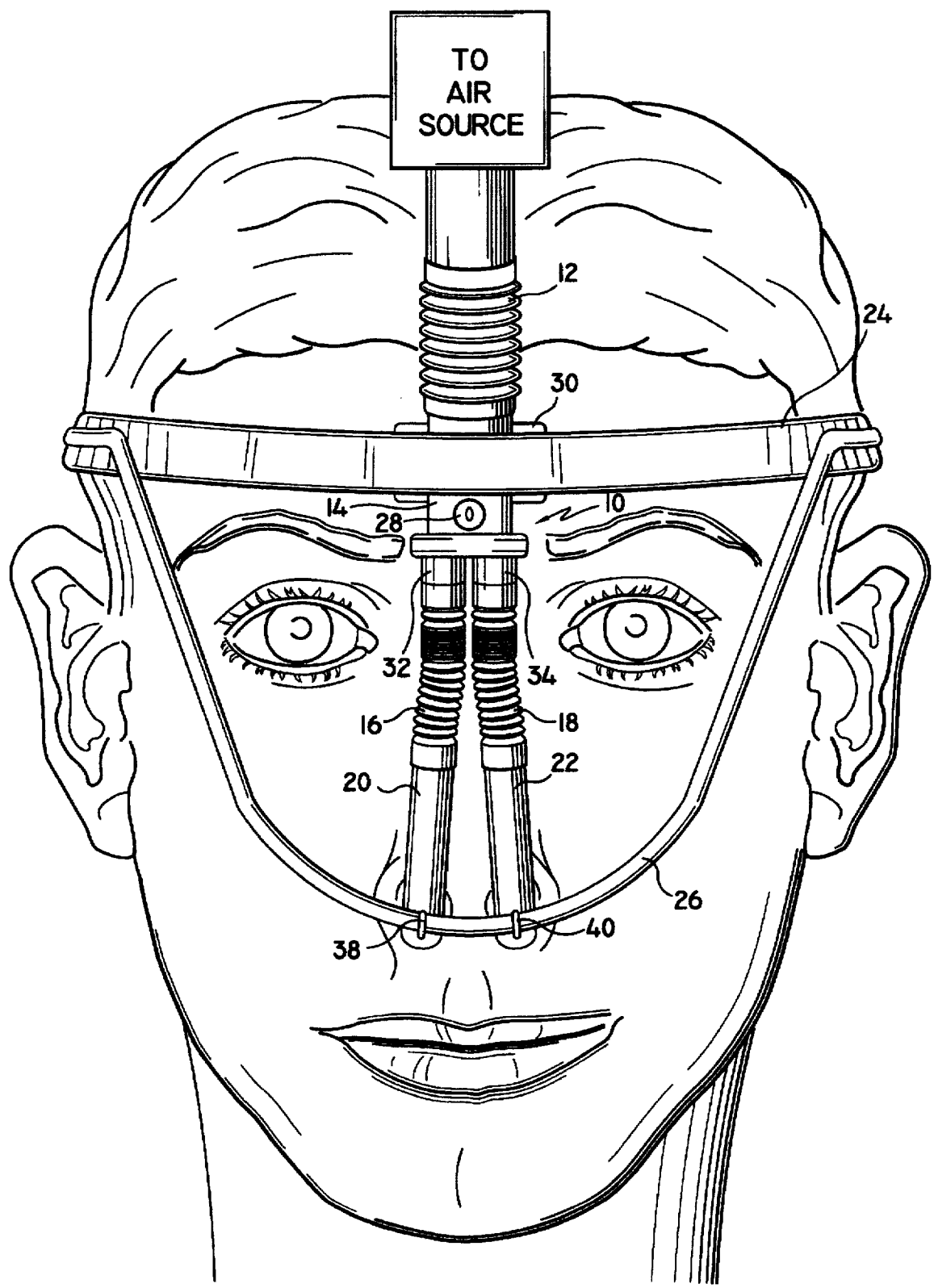
FIG. 1 is a front elevation view of an apparatus in accordance with the disclosure mounted upon the head of a patient, illustrating a variable orifice on the plenum chamber.

As those skilled in the art will appreciate, the foregoing drawings are illustrative only, and show the features of the invention in accordance with the disclosure as they relate to one another. The drawings are not drawn strictly to scale and should be interpreted accordingly.

DETAILED DESCRIPTION OF THE PREFERRED EMBODIMENTS

Referring generally to the drawings, wherein common reference numerals are used to refer to like elements, there is shown a nasal positive airway pressure device 10. Device 10 generally consists of a primary tube 12, a plenum chamber 14, and a pair of nasal tubes 16, 18 connected to nasal delivery elements 20, 22, respectively. The device also oncludes a variable orifice vent aperture member 28. The apparatus may be secured to the head of the user with a head band 24 in a known manner. An adjustable support strap 26 preferably extends from the head band to aid in holding the nasal members adjacent the nose of the user. As will be explained in greater detail below, the nasal delivery elements connected to the plenum chamber extend adjacent to and in communication with the nares of a patient to deliver pressurized air to effect treatment.

FIG. 1 is a front elevation view of a positive airway pressure device constructed in accordance with the disclosure mounted to the head of a user. Primary tube 12 is made of a relatively flexible adjustable material, such as plastic, and is connected to a source of pressurized gas, as schematically illustrated. The source of pressurized gas may be any source suitable for treating sleep apnea, and may be a source of pressurize air with or without supplements such as oxygen. The source of gas may provide continuous pressure as used in nCPAP treatment, or may provide varied levels of pressure such as used in BiPAP™ treatment. In either case, the gas pressure typically is in the range of about 5 to about 15 centimeters of water. As shown in FIG. 1, primary tube 12 may be corrugated in whole or in part to facilitate adjustment. Primary tube 12 typically would have an outer diameter of about 0.25 to 0.375 inches with an inner diameter of about 0.25 inches.

Referring again to FIG. 1, primary tube 12 is attached to plenum chamber 14. A head band 24 holds the device in place relative to the user's head, preferably by engaging the plenum chamber. As shown, a foam or other cushioned pad 30 may be placed between the plenum chamber and the forehead of the user for added comfort. As will be appreciated, pad 30 may be pre-attached to plenum chamber 14 for ease of use. Headband 24 preferably is a cloth or plastic strap with a simple fastening structure such as a hook and loop fastener, e.g., a Velcro™ fastener. As shown in FIG. 1 and described in greater detail below, a variable orifice member 28 is provided on the plenum chamber. Plenum chamber 14 also has a pair of nasal delivery element connectors 32, 34 extending therefrom and adapted to be connected to nasal tubes 16, 18. As shown, plenum chamber 14 preferably is positioned adjacent the forehead of the user. Plenum chamber 14 preferably is made of a substantially rigid material, such as rigid plastic or metal. Suitable plastics include homopolymers, copolymers, blends and mixtures of polystyrene, ABS, polycarbonate, acrylics, polyethylene, polyethylene terathalate, polybutylene, polybutylene terathalate and others. Suitable metals include stainless steel, titanium, aluminum and alloys thereof. As shown, nasal tubes 16, 18 are connected to nasal delivery element connectors 32, 34 so as to maintain gas pressure, such as by friction or snap fit, gluing, welding, etc. Preferably, nasal delivery element connectors 32, 34 are spaced apart by a center-to-center distance approximating the center-to-center distance between the nares of an average user, such as about one(1) centimeter. Spacing the nasal delivery element connectors by this distance facilitates adjustment of the device for optimal patient comfort. Nasal tubes 16, 18 preferably are made of a flexible plastic material, and may be made of corrugated expandable plastic tubing made from polypropylene provided in a compact state to be expanded by the user for adjustment of the device. The proximal ends of nasal tubes 16, 18 are connected to nasal delivery element connectors 32, 34, respectively. The distal ends of nasal tubes 16, 18 are connected to nasal delivery elements 20, 22, also in a manner to preserve gas pressure, such as by friction or snap fit, gluing, welding, etc.

Nasal delivery elements 20, 22 also may have strap-receiving hook members 38, 40 adapted to receive a portion of a strap 42 to further support the nasal members in the nares of the patient. As shown, strap 42 is adjustably secured to headband 24, such as by hook and loop fasteners.

Figure 2:
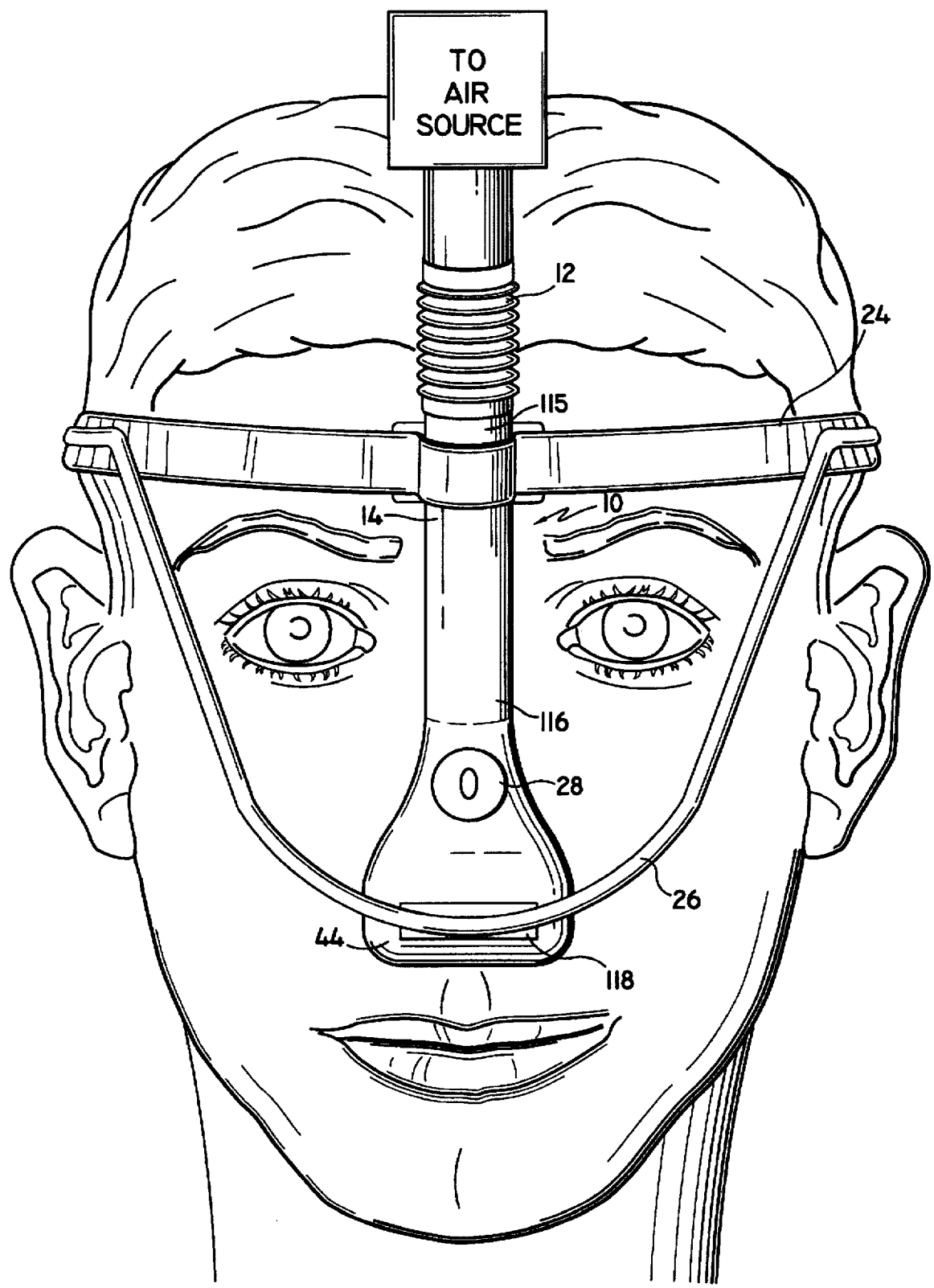
FIG. 2 is a front elevation view of an apparatus in accordance with the disclosure mounted upon the head of a patient, illustrating a variable orifice on an alternative plenum chamber.
Figure 3:
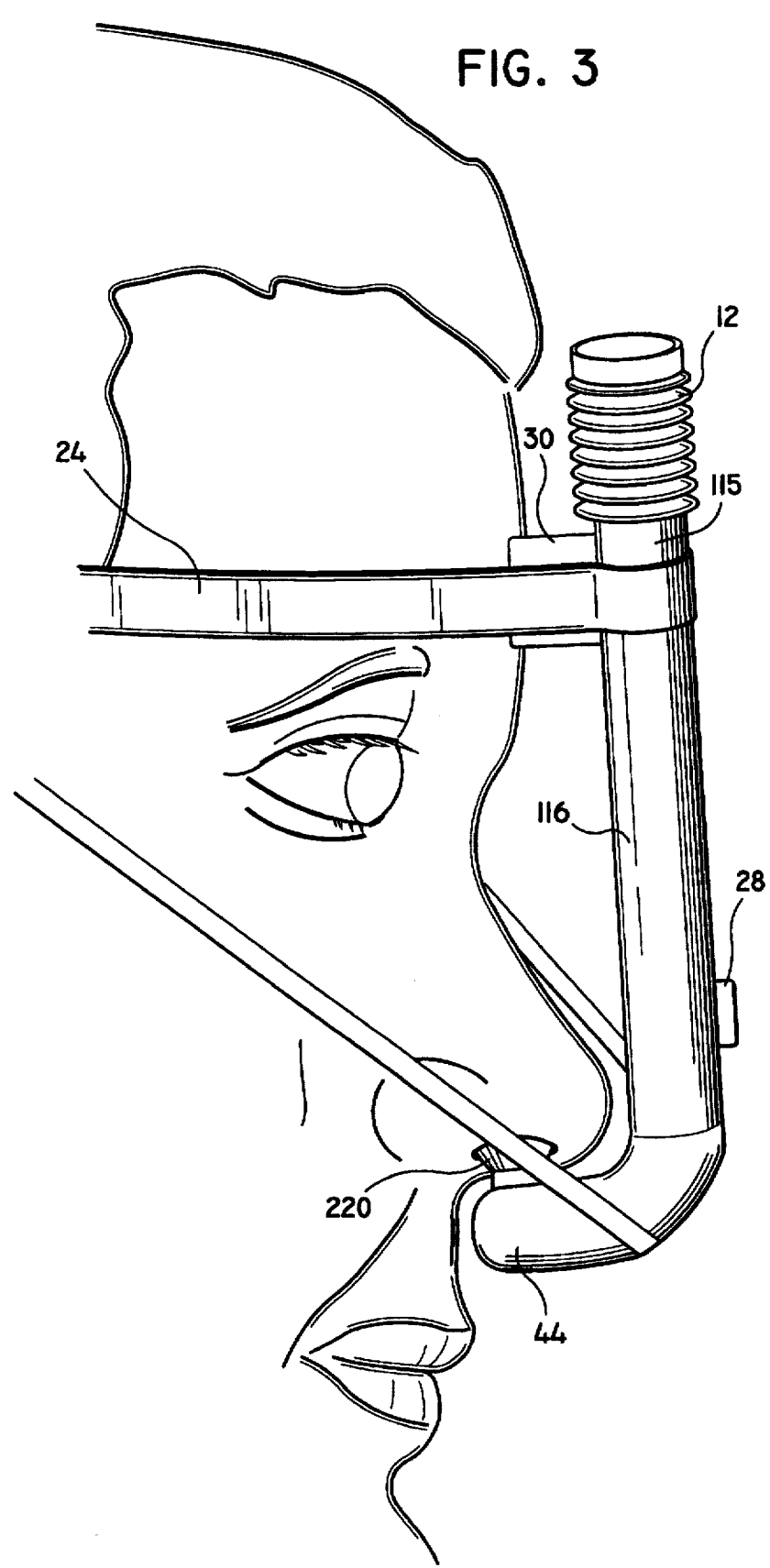
FIG. 3 is a partial side view of the apparatus of FIG. 2 mounted upon the head of a patient.

An alternative plenum chamber configuration is shown in FIG. 2. Primary tube 12 is connected to an air source and to plenum chamber 114 in the same manner as in FIG. 1. As shown, however, plenum chamber 114 is configured as a single unit extending from the connection to primary tube 12 to the patient's nostrils. Nasal delivery elements (not shown in FIG. 2) are connected to plenum chamber 114 and communicate with the patient's nostrils. As in the configuration shown in FIG. 1, variable orifice vent aperture member 28 is mounted to the plenum chamber. FIG. 3 is a partial side view of the apparatus of FIG. 2, illustrating the plenum chamber 114 positioned adjacent the patient's nose with the nasal delivery elements, one of which is partially visible as nasal delivery element 220, extending into and communicating with one nostril. As shown, plenum chamber 114 may be held in place, at least in part, by strap 42. In FIG. 2, however, strap 42 is fastened to plenum chamber 114 by hook and loop fasteners rather than by engaging molded hooks (compare FIG. 1).

Figure 4:
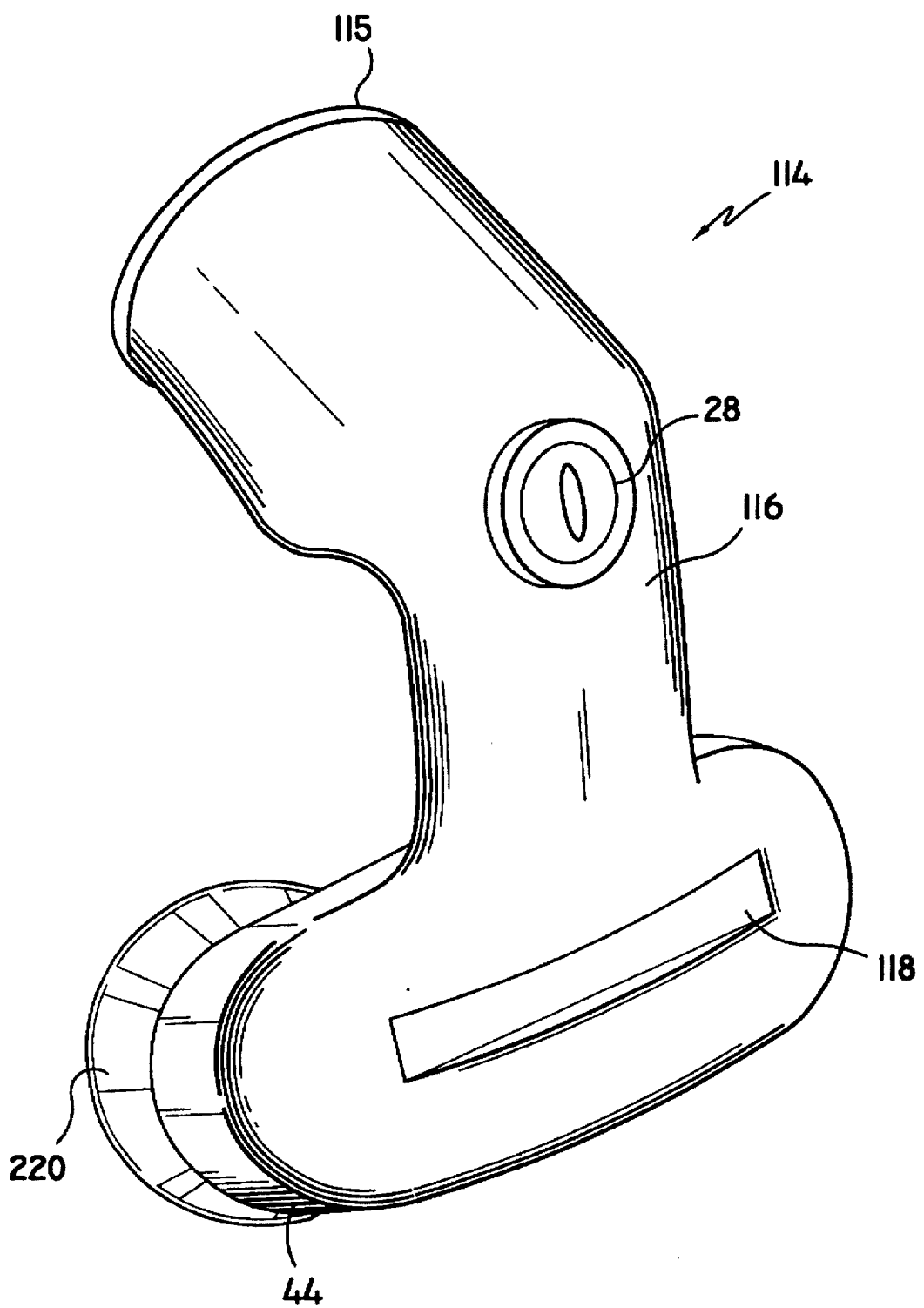
FIG. 4 is a perspective view of the apparatus shown in FIG. 2.

FIG. 4 is a perspective view of plenum 114 of FIG. 2. Plenum chamber 114 includes a primary tube connection 115, a plenum body 116, and a hook and loop fastener 118 to engeage strap 42 (see FIG. 3). Nasal delivery element 120 is partially visible in FIG. 4 extending from the plenum. Variable orifice member 28 is shown mounted to the plenum body 116.

Figure 5:
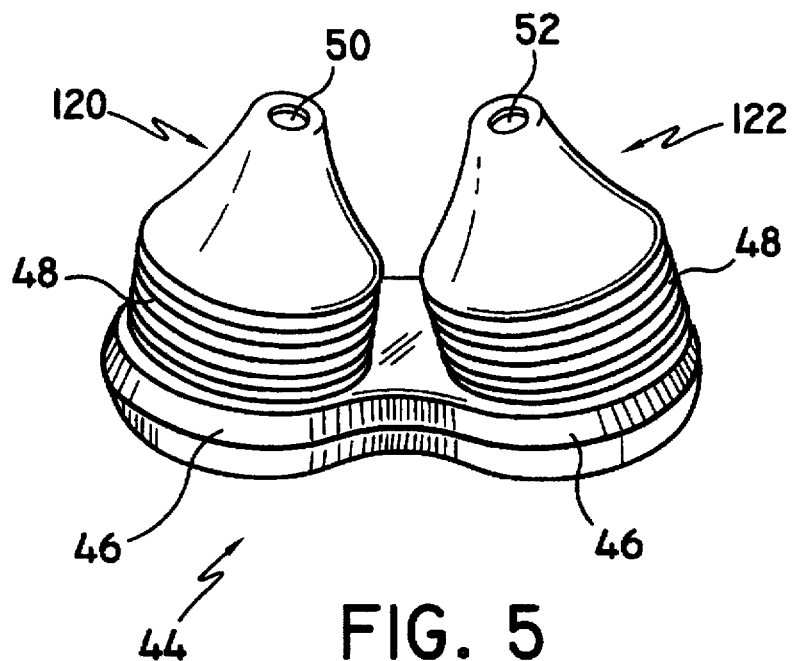
FIG. 5 is an elevation view of a nasal delivery system which can be used with the device shown in FIGS. 1 and 2.
Figure 6:
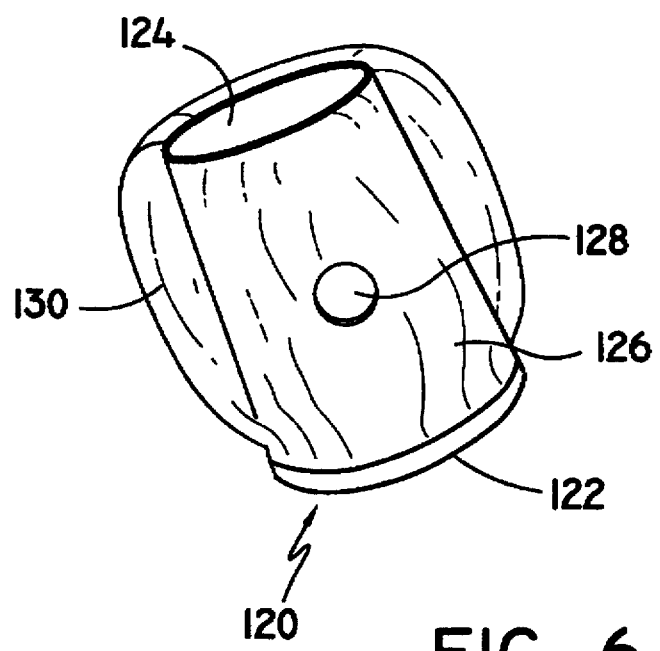
FIG. 6 is a perspective view of a nasal tip member consisting of a cannula and an inflatable cuff (illustrated in the inflated condition), a pair of which can be used as the nasal delivery elements of the devices shown in FIGS. 1 and 2.

Nasal delivery elements useful with either of the plenum arrangements shown in FIGS. 1–4 will now be described. In this regard, FIG. 5 is a front perspective view of the nasal delivery portion 44 of plenum chamber 114 (FIG. 4) having a pair of compliant, generally frustoconical nasal delivery elements 120, 122 mounted thereto. FIG. 6 illustrates an alternative nasal delivery element 220 consisting of a cannula 126 surrounded by an inflatable cuff 130. The interior of cuff 130 communicates with the lumen of cannula 126 through aperture 128. As will be appreciated, the nasal delivery elements shown in FIGS. 5 and 6 may be used with either of the device configurations shown in FIGS. 1 and 2. In addition, other suitable nasal delivery element configurations may occur to those skilled in the art.

Referring to FIG. 5, nasal delivery portion 44 includes a pair of laterally diverging hollow outlet legs 46 in communication with the hollow body of plenum chamber 114. Nasal delivery elements 120, 122 are connected to outlet legs 46 in sealing engagement therewith, and may if desired be mounted in slots on legs 46 to provide further lateral adjustment. Elements 120, 122 are flexible and conform to the shape and orientation of the user's nose. The nasal delivery elements in FIG. 5 are generally frustoconical in shape and are made of a soft, compliant material, e.g., silicone or poyurethane, to conform to the shape of the patient's nares openings and form a seal therewith. Elements 120, 122 are shown having a bellows section 48 for added flexibility and comfort. The tip of teh frustoconical elements have openings 50, 52 respectively. Because the nasal delivery element is hollow and communicates with the hollow interior of plenum 114, pressurized air is conveyed by the plenum to nasal delivery elements which, in turn, deliver the air through openings 50, 52 to the nares to effect treatment. The shape, configuration, mounting and material of elements 120, 122 can be altered and adjusted as described in Trimble U.S. Pat. No. 4,782,832 and known in the art.

An alternative nasal delivery element 220 is shown in FIG. 6. Only the tip of nasal delivery element 220 is shown in FIG. 6. Such a tip portion may be mounted directly to a plenum, such as plenum 114, or may be extended to be attached to nasal tubes 16, 18 (see FIG. 1). As shown in FIG. 6, nasal delivery element 220 has a first, proximal end 122 to engage and be connected to plenum chamber 114 or, alternatively, extensions of nasal tubes 16, 18. Such connections may be by friction fit or other suitable attachment. Element 220 also has a second, distal open end 124. Element 220 includes a cannula 126 having at least one aperture 128 through a sidewall thereof intermediate the first and second ends, and an inflatable cuff 130 surrounding at least a portion of the cannula overlying and enclosing aperture 128. In FIG. 12, inflatable cuff 130 is shown in an inflated condition. Cuff 130 preferably is made from a substantially inelastic polyurethane material. Cannula 126 and inflatable cuff 130 are configured and dimensioned to be inserted into a patient's nares. In FIG. 6, cannula 126 and aperture 128 are visible through a transparent cuff 130. Of course, cuff 130 may also be opaque or pigmented to a particular color, if desired. As also shown in FIG. 6, inflated cuff 130 extends slightly beyond distal open end 124 of the cannula. Cannula 126 may be of substantially circular cross-section at the proximal end, and taper to a substantially oval cross-section at the distal end thereof. Alternaively, cannula 126 may be substantially cylindrical, or may have an oval or eliptical open distal end. Further details of such configurations are set forth in parent U.S. Pat. No. 5,477,852, which has been incorporated herein by reference.

As shown throughout the figures, the device includes a variable orifice vent aperture member 28. Variable orifice vent aperture member 28 preferably is mounted to the plenum chamber, as shown in FIGS. 1–3, although it is contemplated that the variable orifice member may be mounted to the primary tube, nasal tube, or other similar conduits or connectors adjacent the patient's nose. In one construction, variable orifice vent aperture member 28 is configured as a cap to mount onto and engage projecting walls of a cylindrical opening in the plenum chamber (not shown). This is just one method of mounting the variable orifice vent aperture member to the device, and other structures and methods will occur to those skilled in the art with practice.

Referring now to FIGS. 7A–7D, the variable orifice cap 28 is shown in greater detail. FIG. 7A is a perspective view of the variable orifice cap having vertical side walls 60 and aperture defining surface 62. The variable orifice cap is shown in FIG. 7A in the first, unexpanded state defining aperture 64' having a first, reduced diameter. Referring now to FIG. 7B, aperture defining surface 62 is shown in a second, expanded state defining an expanded aperture 64" having a second diameter which is larger than the diameter of 64'. FIG. 7C is a perspective sectional view of the variable orifice cap of FIG. 7A shown in the unexpanded state. As shown, side walls 60 have a first thickness sufficient to give rigidity to the cap and frictionally engage a cylindrical projecting wall on the device. As shown, aperture defining surface 62 is of substantially reduced thickness compared to side wall 60, and may taper from a first thickness at a point 66 adjacent side wall 66 to a very thin, flexible thickness 68 immediately adjacent aperture 64'. Referring now to FIG. 7D, a perspective section view of the variable orifice cap of FIG. 7B showing aperture defining surface 62 in the expanded state, the aperture defining surface 62 is expanded in the area adjacent the aperture to define larger expanded aperture 64". More particularly, the reduced thickness portion 68 of surface 62 stretches under pressure to expand the diameter of the aperture. At least the aperture defining surface 62 of variable orifice cap 28 may be made of a flexible material capable of expanding and contracting, such as latex rubber.

In use, the variable orifice cap is mounted over and onto the projecting wall of the plenum. The nasal delivery elements are placed into the patient's nostrils and the source of pressurized air is activated. During inhalation the pressure at the orifice cap is at a minimum level and the aperture defining surface 62 is in the unexpanded state shown in FIGS. 7A, 7C. During exhalation the gas pressure at orifice cap increases and exerts pressure upon orifice defining surface 62 to cause the surface to stretch and expand, creating expanded orifice 64" as shown in FIGS. 7B and 7D. The variable orifice cap is an improvement over fixed aperture devices because the first, unexpanded aperture state allows efficient transfer of pressurized gas to the nares of the patient at relatively low pressure during inhalation. Conversely, during exhalation the gas pressure adjacent variable orifice cap substantially increases and the increased pressure causes orfice defining surface 62 to stretch and expand, resulting in the aperture assuming a larger diameter expanded state. This allows exhaled gas to exit the device through the aperture with less resistance than with a fixed orifice device, which typically has an opening on the order of the unexpanded state of the variable orifice. Advantageously, the variable orifice cap may be used with any form of positive nasal airway pressure therapy, e.g. nCPAP or BiPAP™ therapy.

Of course, numerous modifications and alterations to the variable orifice embodiment will occur to those skilled in the art. By way of example only, the stretchable orifice defining surface could be mounted to the nasal member in a variety of ways, such as by mounting the stretchable membrane directly to a surface of the device across an opening, such as by gluing a latex rubber membrane defining the variable orifice to the inside surface of the nasal member over an opening. Similarly, a substantially flat variable orifice defining member could be placed over aperture 64, with a substantially rigid open-centered cap placed over the orifice defining member to capture the orifice defining under the cap. In addition, it will be understood that the variable orifice member can be positioned at other locations than shown in the Figs., as long as the variable orifice member is placed reasonably close to the patient's nares along the path of the gas supply to the nares. These and other modifications will occur to those skilled after learning of and practicing the invention.

Device 10 may be fabricated in whole or in part from disposable or reusable plastics such as ABS plastic, polystyrene, polyethylene terathalate, polycarbonate, polyurethanes, polyesters, polypropylene, polyethylene, acrylics, etc. and may be fabricated by any suitable techniques such as blow or injection molding, extrusion, grinding cutting etc. The entire device may be disposable, or only parts of the instrument may be disposable. For example, all parts other than the nasal delivery members might be relatively permanent with only the nasal delivery members being periodically replaced.

The foregoing description contains many specifics and numerous alternative structures and combinations will occur to those skilled in the art. As previously stated, for example, it is contemplated that a plurality of variable orifice vent apertures may be provided at various locations on the device to achieve substantially the same results. These and numerous other changes, variations and improvements will occur to those skilled in the art with practice of the invention claimed in the accompanying claims.

What is claimed is:

1. A device for treatment of sleep apnea comprising:
  a source of pressurized air;
  a plenum chamber in communication with the source of pressurized air;
  a pair of nasal delivery members connected to and in communication with the plenum chamber, the nasal delivery members being configured and dimensioned to delivery pressurized air from the plenum to the nares of a patient;
  at least one variable orifice member defining a variable orifice which assumes a first position having a first diameter at a first gas pressure and a second, expanded position having a second diameter greater than said first diameter at a second, increased gas pressure.

2. The device of claim 1 wherein the variable orifice member is mounted to the plenum.

3. The device of claim 1 wherein the plenum is connected to the source of pressurized air by a primary air tube.

4. The device of claim 1 wherein the variable orifice member is mounted to the primary air tube.

5. The device of claim 1 wherein the variable orifice member is mounted to the nasal delivery members.

6. The device of claim 1 wherein the variable orifice member comprises a stretchable material having an aperture therethrough.

7. The device of claim 1 further comprising means for mounting the plenum to the head of a patient.

8. The device of claim 1 further comprising a pair of nasal tubes connecting the nasal members to the plenum.

9. The device of claim 1 wherein the source of pressurized air is a source of substantially constant pressure air.

10. The device of claim 1 wherein the source of pressurized air provides at least two different pressure conditions of air.

11. The device of claim 1 wherein the nasal delivery members include a pair of generally frustoconical tips.

12. The device of claim 11 wherein the generally frustoconical tips are made of a compliant synthetic material.

13. The device of claim 1 wherein the nasal delivery members comprise a cannula having at least one aperture through the side wall of the cannula and an inflatable cuff secured to the outer surface of the cannula surrounding at least a portion of the cannula and overlying the aperture, the cannula and inflatable cuff configured and dimensioned for insertion into a patient's nares.

14. The apparatus of claim 13 wherein said inflatable cuff is made of a substantially inelastic material.

15. The apparatus of claim 14 wherein said inelastic material is polyurethane.

16. The device of claim 13 wherein the cannula is tapered.

17. A device for treatment of sleep apnea comprising:
  a source of pressurized air;
  a plenum chamber in communication with the source of pressurized air;
  a pair of nasal delivery members connected to and in communication with the plenum chamber, each nasal delivery member including a cannula having at least one aperture through the side wall of the cannula and an inflatable cuff secured to the outer surface of the cannula surrounding at least a portion of the cannula and overlying the aperture, the cannula and inflatable cuff configured and dimensioned for insertion into a patient's nares.

18. The device of claim 17 further comprising at least one variable orifice member defining a variable orifice which assumes a first position having a first diameter at a first gas pressure and a second, expanded position having a second diameter greater than said first diameter at a second, increased gas pressure.

19. The device of claim 18 wherein the variable orifice member is mounted to the plenum.

20. A method of treating for sleep apnea comprising:

connecting a source of pressurized air to a plenum chamber, the plenum chamber having a pair of nasal delivery members connected to and in communication with the plenum chamber configured and dimensioned for insertion into the nares of a patient, the plenum further including at least one variable orifice member defining a variable orifice which assumes a first position having a first diameter at a first gas pressure and a second, expanded position having a second diameter greater than said first diameter at a second, increased gas pressure;

inserting the nasal delivery elements into the nares of a patient;

activating the source of pressurized air to supply positive air pressure to the nasal delivery element through the plenum, the variable orifice member assuming the first diameter during inhalation by the patient and the second, enlarged diameter during exhalation by the patient.

* * * * *